US010264755B2

(12) United States Patent
Valera Rojas et al.

(10) Patent No.: US 10,264,755 B2
(45) Date of Patent: Apr. 23, 2019

(54) SOYBEAN VARIETY SM14307266

(71) Applicant: Agrigenetics, Inc., Indianapolis, IN (US)

(72) Inventors: Evelyn Valera Rojas, London (CA); Kari Greason, London (CA)

(73) Assignee: Agrigenetics, Inc., Indianapolis, IN (US)

( * ) Notice: Subject to any disclaimer, the term of this patent is extended or adjusted under 35 U.S.C. 154(b) by 0 days.

(21) Appl. No.: 15/827,093

(22) Filed: Nov. 30, 2017

(65) Prior Publication Data

US 2018/0153120 A1 Jun. 7, 2018

Related U.S. Application Data

(60) Provisional application No. 62/428,827, filed on Dec. 1, 2016.

(51) Int. Cl.
*A01H 5/10* (2018.01)
*A01H 6/54* (2018.01)
*A01H 1/02* (2006.01)
*C07K 14/325* (2006.01)

(52) U.S. Cl.
CPC ............... *A01H 6/542* (2018.05); *A01H 1/02* (2013.01); *A01H 5/10* (2013.01); *C07K 14/325* (2013.01)

(58) Field of Classification Search
None
See application file for complete search history.

(56) References Cited

U.S. PATENT DOCUMENTS 9,271,463 B1 * 3/2016 Gilsinger ................. A01H 5/10

\* cited by examiner

*Primary Examiner* — Elizabeth F McElwain

(57) ABSTRACT

Disclosed is the seed of a novel soybean variety, designated SM14307266, a sample of which is deposited under ATCC Accession No. PTA-123574. Also disclosed are plants, or parts thereof, grown from the seed of the variety, plants having the morphological and physiological characteristics of the SM14307266 variety, and methods of using the plant or parts thereof in a soybean breeding program.

24 Claims, No Drawings

SOYBEAN VARIETY SM14307266

CROSS-REFERENCE TO RELATED APPLICATION

This application claims priority to U.S. Provisional Patent Application Ser. No. 62/428,827, filed Dec. 1, 2016, the disclosure of which is hereby incorporated herein in its entirety by this reference.

FIELD OF THE DISCLOSURE

This invention relates generally to the field of soybean breeding. In particular, the invention relates to a soybean variety designated SM14307266 that includes plants, plant parts, and seeds of soybean variety SM14307266. Methods for producing soybean plants by crossing soybean variety SM14307266 with itself or any different soybean plant are an integral part of this invention as are the resultant soybean plants, including the plant parts and seeds. This invention further relates to methods for producing SM14307266-derived soybean plants and to methods for regenerating such plants from tissue cultures of regenerable cells as well as the plants obtained therefrom. Methods for producing a soybean plant containing in its genetic material one or more transgenes and to the transgenic soybean plants produced by that method are also a part of this invention.

BACKGROUND

Soybean (*Glycine max*) is a major grain crop valued for the high levels of oil and protein found in soybean seed. Soybean breeding has resulted in significant improvements in yield potential, stability of yield, adaptation of the species to mechanical harvest, and yield protection through improved disease resistance.

Due to the nature of plant science agriculture, broadly defined as a manipulation of available plant resources to meet the needs of the growing human population, the environment in which plants are grown for agricultural production continuously offers new obstacles to agricultural production. Each new variety, or cultivar, released to agricultural production is selected for the purpose of increasing yield resulting from increased disease resistance to prevalent diseases, or from direct or indirect improvement in yield potential or efficiency of production. Development of stable, high yielding varieties with superior characteristics is an ongoing goal of soybean breeders.

There is a need in the art for a novel, superior soybean variety and soybean seed.

SUMMARY

In one aspect, the present invention provides a soybean seed designated SM14307266, wherein a sample of said seed is deposited under ATCC Accession No. PTA-123574.

In another aspect, the present invention provides a soybean plant, or a part thereof, produced by growing seed designated SM14307266, or a soybean plant having all the physiological and morphological characteristics of the soybean plant when grown in the same environmental conditions, or a pollen grain, an ovule, a protoplast, a cell, an embryo, a cotyledon, a hypocotyl, a meristem, a root, a pistil, an anther, a flower, a stem, a pod, a leaf, or a petiole of a soybean plant according to the present invention.

In yet another aspect, the present invention provides a tissue culture of protoplasts or regenerable cells from a plant, or parts thereof, produced by growing seed designated SM14307266, and a soybean plant regenerated from the tissue culture.

In still another aspect, the present invention provides a method for producing a soybean seed, and soybean seed produced by the method, as well as plants grown from seed produced by the method are provided. The method comprises crossing soybean plants and harvesting the resultant seed, wherein at least one soybean plant is the soybean variety SM14307266 of the present invention.

In another aspect, a method for producing a soybean variety SM14307266-derived soybean plant, and soybean variety SM14307266-derived soybean plants, or parts thereof, produced by the methods are provided. The method comprises crossing a soybean variety SM14307266 plant of the present invention with a second soybean plant to yield F1 hybrid progeny soybean seed and growing the progeny seed to yield an F1 soybean variety SM14307266-derived soybean plant. In some embodiments, the method further comprises crossing the soybean variety SM14307266-derived soybean plant with itself or another soybean plant to yield an additional soybean variety SM14307266-derived soybean progeny seed and growing this progeny soybean seed to yield additional soybean variety SM14307266-derived soybean plants. In some embodiments, these last two steps are repeated at least one time to generate additional soybean variety SM14307266-derived soybean plants.

In yet another aspect, a method for producing a plant of soybean variety SM14307266 comprising an added desired trait, and plants produced by the method, are provided. In some embodiments, the method comprises introducing at least one transgene or locus conferring the desired trait into the soybean variety SM14307266 plant. In certain embodiments, the desired trait is selected from the group consisting of male sterility, site-specific recombination, abiotic stress tolerance, herbicide tolerance, insect or pest resistance, disease resistance, fungal resistance, modified fatty acid metabolism, modified protein metabolism, and modified carbohydrate metabolism. In other embodiments, the desired trait is herbicide tolerance and the tolerance is conferred to one or more herbicides selected from the group consisting of glyphosate, phenoxyacetate auxins (such as 2,4-diclorophenoxyacetic acid (2,4-D)), pyridyloxyacetate auxins (such as fluroxypyr and triclopyr), phenoxyproprionate auxins (such as MCPA and dichloprop), phenoxybutanoate auxins (such as 2,4-DB), sulfonylurea, imidazalinone, dicamba, glufosinate, cyclohexone, triazine, and benzonitrile. In still other embodiments, the desired trait is insect resistance and the transgene encodes a *Bacillus thuringiensis* (Bt) endotoxin.

In still another aspect, a method of producing a progeny soybean variety derived from variety SM14307266 comprising a desired trait, and plants produced by the method, are provided. In some embodiments, the method comprises crossing a soybean variety SM14307266 plant of the present invention with a plant of another soybean variety that comprises a desired trait to produce F1 progeny plants, selecting one or more F1 progeny plants that have the desired trait to produce selected progeny plants, crossing the selected progeny plants with the SM14307266 plants to produce backcross progeny plants, selecting for backcross progeny plants that have the desired trait and physiological and morphological characteristics of soybean variety SM14307266 to produce selected backcross progeny plants, and repeating the last two steps a sufficient number of times in succession to produce selected second or higher backcross progeny plants that comprise the desired trait and the physiological and morphological characteristics of soybean variety SM14307266 when grown in the same environmental conditions. In some embodiments, the last two steps are repeated three or more times in succession to produce selected fourth or higher backcross progeny plants. In some embodiments, the desired trait is selected from the group consisting of male sterility, herbicide tolerance, insect resistance, modified fatty acid metabolism, modified carbohydrate metabolism, and resistance to bacterial disease, fungal disease or viral disease.

In yet another aspect, a method of producing a commodity plant product is provided, which comprises obtaining a plant of the present invention, or a part thereof, and producing the commodity plant product therefrom. In some embodiments, the commodity plant product is protein concentrate, protein isolate, soybean hulls, meal, flour or oil.

DETAILED DESCRIPTION

In the claims, descriptions, and tables that follow, numerous terms are used and are defined as follows:

Brown Stem Rot (BSR) caused by the fungus, *Phialophora gregata*, is visually scored from 1 to 9 based on the severity of interveinal leaf chlorosis (yellowing) and necrosis of stems. A score of 1 indicates the most resistance (no symptoms) and a score of 9 indicates the most susceptible.

Canopy width is measured at the widest point of the soybean plant. Visually scored from 1 to 9, where 1=very narrow canopy and 9=extremely bushy canopy.

Cotyledon is a type of seed leaf. The cotyledon contains the food storage tissues of the seed. Cotyledon color can be measured as a characteristic of a variety.

Flower color: Modern soybeans are characterized by two major flower colors, purple or white. Some varieties are heterogeneous for flower color whereby some plants have purple flowers and some have white.

Growth habit refers to stem termination in soybeans and the resultant differences in flower production. "Indeterminate" varieties continue to grow during the reproductive phase, producing new branches and nodes after flowering is well underway. "Determinate" varieties tend to delay the onset of flowering somewhat, and limit new node and branch development after flowering has been initiated. "Semi-determinate" varieties continue to produce new vegetative growth during the reproductive phase but growth terminates more quickly than in indeterminate varieties.

Hilum refers to the point of attachment of soybean seed to maternal tissue.

Hilum color in modern soybeans may be black, brown, yellow, gray, buff, or imperfect black.

Iron-Deficiency Chlorosis (IDC) results when soybeans lack adequate iron. A visual score taken 25 to 30 days after planting is used to rate iron-deficiency chlorosis. A score of 1 indicates no stunting of the plants or chlorosis of the leaves, and a score of 9 indicates the plants are dead or dying as a result of iron-deficiency chlorosis. A score of 4.5 means plants have intermediate health with some leaf chlorosis.

Leaflet shape: The leaflet may be broad or narrow and may be lanceolate, ovate or oval in shape.

Lodging relates to the stature of the plant relative to the ground. Lodging resistance is rated on a scale of 1 to 5. A score of 1 is given to an erect plant (lodging resistant). A score of 3 is given to a plant that is leaning at a 45-degree angle relative to the ground. A score of 5 indicates a plant lying on the ground.

Maturity date is the date when 95% of pods have turned color from green color to their mature brown or tan color. The maturity date is counted in days and is calculated from January 1.

Maturity group refers to an industry division of groups of varieties based on the zones in which the varieties are adapted. Soybeans mature differentially in response to day-length and thus to latitude where grown. In the soybean production areas of the United States, for example, the northernmost production region of northern Minnesota is planted to soybeans that mature under very long day-lengths during early summer. In the southernmost production regions of the Southeast, soybeans that mature from the influence of short day-length during early summer are grown. Those adapted to northern day-lengths are classified as early-maturing, those adapted to the southern regions are classified as late-maturing. Maturity groups include very long day length varieties (000, 00, 0) and extend to very short day length varieties (VII, VIII, IX, X). For example, maturity group I soybean varieties are typically grown in southern Minnesota, whereas maturity group IV soybean varieties are typically group in southern Illinois.

*Phytophthora* "Root Rot" tolerance caused by the fungus, *Phytophthora megasperma* var. *sojae*, is rated on a visual scale of 1 to 9, with a score of 1 being the most tolerant and a score of 9 s being the most susceptible to *Phytophthora*. The visual score is based on the amount of disease-induced stunting of above-ground growth and is taken at harvest.

Plant includes plant cells, plant protoplasts, plant cell tissue cultures from which soybean plants can be regenerated, plant calli, plant clumps, and plant cells that are intact in plants or parts thereof. "Plant part" includes, but is not limited to, embryos, protoplasts, cells, pollen, ovules, cotyledons, hypocotyls, meristems, roots, pistils, anthers, flowers, stems, leaves, pods, petioles, and the like.

Plant height is measured from the top of soil to top node of the plant in any convenient unit of length (i.e., inches, centimeters, etc.). For the data presented herein, plant height was measured just prior to harvest and is expressed in centimeters.

Pod wall color refers to the color of the mature pod wall, as distinct from the color of the pubescence, and in modern soybeans, may be brown or tan.

Pubescence relates to the plant trichomes or hairs found on the stems, leaves and pods of soybeans.

Pubescence color in modern soybeans may be tawny, gray or light tawny.

Relative maturity, within maturity groups, is a more precise maturity assignment that subdivides each maturity group into tenths. For example, a relative maturity of 3.3 is assigned to a late early maturity group III soybean variety.

Roundup Ready 2 tolerance refers to the transgenic soybean event MON89788 from Monsanto Company, as identified in the USDA petition extension No 06-1780-01p, which imparts glyphosate tolerance to the plant.

*Sclerotinia* Stem Rot, also referred to as "white mold", is caused by the soil-borne fungus, *Sclerotinia sclerotiorum*. Plants are infected via discharged ascospores that successfully germinate and infect through soybean structures such as flower petals. Colonization of stem, pod, and leaf tissue ultimately results in loss of yield potential. Cultivars are rated based on prevalence and severity of a 1 to 9 scale, with 1 being no infection and 9 being severe infection.

Seed coat color refers to the color of the seed coat, and in modern soybeans may be yellow, green, brown or black.

Seed coat luster refers to the luster of the seed coat, and may be dull or shiny.

Seed coat peroxidase activity is defined by a chemical taxonomic technique to separate varieties based on the presence or absence of the peroxidase enzyme in the seed coat. There are two types of soybean varieties, those having high peroxidase activity and those having low peroxidase activity. Ratings are HIGH or LOW for peroxidase enzyme activity.

Seed size is measured by seed number per pound of seed. Seed size is a heritable trait but is influenced by environment, and as such, is often presented as a comparison to another variety.

Shattering refers to pod dehiscence prior to harvest resulting in a loss of mechanically harvestable seed. Pod dehiscence involves seeds falling from the pods to the soil. This is visually scored with a 1 to 9 scale comparing all genotypes within a given test. A score of 1 means pods have not opened and no seeds have fallen out. A score of 5 indicates approximately 50% of the pods have opened, with seeds falling to the ground and a score of 9 indicates 100% of the pods are opened.

Soybean Cyst Nematode (SCN) resistance is based on a comparison of reproduction rates of *Heterodera glycines* to a known susceptible variety as described by Schmitt et al. (Crop Sci. 32:275-277, 1992), which is incorporated by reference herein. A variety with a 0% to 10% reproductive rate compared to a known susceptible variety is classified as resistant (R); a variety with an 11% to 30% reproductive rate compared to a known susceptible variety is classified as moderately resistant (MR); a variety with an 31% to 59% reproductive rate compared to a known susceptible variety is classified as moderately susceptible (MS).

Soybean emergence scores, also referred to simply as "Emergence," rate the ability of the seedlings to emerge from the soil. A visual score of 1 to 9, taken from emergence to V3, is used whereby a score of 1 to 3 indicates excellent emergence vigor and early growth, an intermediate score of 5 indicates average ratings, and a score of 7 to 9 indicates a very poor emergence vigor and early growth.

Sulfonylurea Tolerance is a herbicide-tolerance trait that improves soybean tolerance to ALS (acetolactate synthase) inhibitor herbicides. Sulfonylurea Tolerant soybeans carry a modified ALS gene, which enhances the variety's natural tolerance to sulfonylurea.

Yield refers to the yield of seed harvested from a soybean crop. Yield data presented herein is expressed as bushels of seed/acre and is the actual yield of the grain at harvest.

Soybean Variety SM14307266

The present invention provides plants, seeds, plant parts, and derivatives thereof of the soybean variety SM14307266, characterized by molecular and physiological data obtained from the representative sample of said variety deposited with the American Type Culture Collection (ATCC). The present invention further provides methods for producing soybean variety SM14307266 and methods for breeding with soybean variety SM14307266 to produce novel derived soybean varieties.

Soybean variety SM14307266 has superior characteristics and was developed from crossing two elite soybean varieties. Some of the criteria used to select the variety in various generations included seed yield, lodging resistance, emergence, disease resistance and tolerance, herbicide tolerance, maturity, late season plant intactness, plant height, and shattering resistance. The breeding history of the variety is summarized in Table 1.

TABLE 1

Breeding Method for Cultivar SM14307266

| Filial Generation | Method |
| --- | --- |
| F0 | cross between parents |
| F1 | plant growout |
| F2 | population growout |
| F3 | progeny row, single-plant selection |
| F4 | plant-row yield trial |
| F5 | preliminary yield trial |
| F6 | purity reselection and seed increase |
| F7 | advanced yield trial |
| F8 | seed increase |
| F9 | advanced yield trial |

Soybean variety SM14307266 has excellent agronomic characteristics including high yield potential relative to lines of similar maturity. Soybean variety SM14307266 is well-adapted to early maturity group II to early maturity group III growing areas of Michigan, Ohio, Indiana, Iowa, Illinois, Minnesota, South Dakota, Nebraska and Wisconsin.

Soybean variety SM14307266 has been judged to have uniformity and stability of its morphological and other characteristics. The variety can be reproduced by planting and growing seeds of the variety under self-pollinating or sib-pollinating conditions, as is known to those of skill in the agricultural arts. Soybean variety SM14307266 shows no variants other than what would normally be expected due to environment or that would occur for almost any characteristic during the course of repeated sexual reproduction. The variety description information (Table 2) provides a summary of soybean variety SM14307266 plant characteristics. Those of skill in the art will recognize that these are typical values that may vary due to environment and that other values that are substantially equivalent are within the scope of the invention. As used herein, "a soybean plant having the physiological and morphological characteristics of soybean variety SM14307266" is a plant having the characteristics set forth in Table 2 when grown in the same environmental conditions.

TABLE 2

Physiological and Morphological Characteristics of Cultivar SM14307266

| Characteristic | Value |
| --- | --- |
| Relative Maturity | 0.09 |
| Maturity Date (days from January 1) | 264 |
| Hilum Color (Mature Seed) | Black |
| Seed Coat Color (Mature Seed) | Yellow |
| Seed Coat Luster (Mature Hand Shelled Seed) | Dull |
| Cotyledon Color (Mature Seed) | Yellow |
| Emergence (1 to 9) | 2 |
| Canopy Width (1 to 9) | 5 |
| Growth Habit | Indeterminate |
| Plant Height (inches) | 30.3 |
| Lodging (1 to 5) | 2 |
| Flower Color | Purple |
| Leaflet Shape | Ovate |
| Pubescence Color | Tawny |
| Pod Wall Color | Tan |
| Shattering (1 to 9) | 1 |
| Resistance/Tolerance to Herbicides | |
| Roundup Ready (40-3-2) | No |
| Roundup Ready 2 (GM_A19788) | Yes |
| Sulfonylurea Tolerant Soybean (STS) | No |
| Resistance/Tolerance to Pests | |
| Soybean Cyst Nematode (R, MR, MS, S) | S |

TABLE 2-continued

Physiological and Morphological Characteristics of Cultivar SM14307266

| Characteristic | Value |
| --- | --- |
| *Phytophthora* Tolerance (1 to 9) | 3 |
| Brown Stem Rot (1 to 9) | 2.5 |
| *Sclerotinia* Stem Rot (1 to 9) | 2 |
| Tolerance to Environments | |
| Iron-Deficiency Chlorosis (1 to 9) | 2.3 |

Soybean variety SM14307266 in one embodiment of the present invention carries one or more transgenes, for example, a glyphosate tolerance transgene, an auxin herbicide (e.g., 2,4-D, dicamba, etc.) tolerance gene, a glufosinate tolerance gene, a desaturase gene or other transgenes. In another embodiment of the invention, the soybean does not carry any herbicide tolerance traits. In yet another embodiment of the invention, the soybean does not carry any transgenes but carries alleles for disease and/or pest resistance, such as aphid resistance, cyst nematode resistance or the like. In still another embodiment, the soybean carries both alleles and transgenes providing desired traits.

In addition to the individual plant characteristics set forth in Table 2, agronomic yield of soybean variety SM14307266 was evaluated. Table 3 compares the yield and maturity difference of soybean variety SM14307266 to those of other soybean varieties developed for a similar crop-production region.

TABLE 3

Yield of Cultivar SM14307266 Compared to Selected Cultivars

| Years (#) | Cultivar | Paired t-test[a] | Reps. (#) | Yield (bu/ac) | Yield (%)[b] | Maturity Difference (days) |
| --- | --- | --- | --- | --- | --- | --- |
| 1 | SM14307266 | NS | 20 | 43.1 | 100 | 0 |
| | AG0333 | −2.4 | | 45.5 | 106 | 7 |
| 1 | SM14307266 | NS | 20 | 43.1 | 100 | 0 |
| | CR0204 | −1.4 | | 44.5 | 103 | 0 |
| 1 | SM14307266 | NS | 20 | 43.1 | 100 | 0 |
| | CR2 00914 | 0.0 | | 43.1 | 100 | 1 |
| 1 | SM14307266 | NS | 20 | 43.1 | 106 | 0 |
| | CR00504 | 2.5 | | 40.6 | 100 | −3 |
| 1 | SM14307266 | ** | 20 | 43.1 | 110 | 0 |
| | AG00932 | 3.9 | | 39.2 | 100 | 1 |

[a]Thresholds for paired t-tests are no significant difference (NS) and significant at P < .05 (*), P < .01 (), and P < .001 (*).
[b]Percentage yield relative to the lower-yielding cultivar in each two-way comparison.

Soybean Variety SM14307266 Breeding and Production Methods

The present invention provides methods for producing soybean seed, or plants grown therefrom, by crossing the soybean variety SM14307266 with itself or a second variety. These methods can be used for propagation of the soybean variety SM14307266, or can be used to produce SM14307266-derived hybrid soybean seeds and the plants grown therefrom. Hybrid soybean plants can be used in the commercial production of soy products or may be advanced in certain breeding protocols for the production of additional novel soybean varieties by crossing the soybean variety SM14307266-derived soybean plant with itself or another soybean plant to yield an additional soybean variety SM14307266-derived soybean progeny seed. This crossing process can be repeated one or more times to generate additional soybean varieties. A hybrid plant can also be used as a recurrent parent at any given stage in a backcrossing protocol during the production of the soybean variety SM14307266 which comprises an added desired trait.

In some embodiments, the present invention provides for using the SM14307266 soybean plant, or part thereof, or a soybean plant having the physiological and morphological characteristics of the SM14307266 soybean plant, as a source of breeding material for developing an SM14307266-derived soybean plant in a soybean breeding program using plant breeding techniques. Plant breeding techniques useful in the developing soybean plants include, but are not limited to, single seed descent, modified single seed descent, recurrent selection, reselection, mass selection, bulk selection, backcrossing, pedigree breeding, mutation breeding, restriction fragment length polymorphism enhanced selection, genetic marker enhanced selection, making double haploids and transformation. Plant breeding techniques are known to the art and have been described in the literature. For example, see U.S. Pat. Nos. 6,143,954; 7,803,996; and 7,807,884, which, along with the references cited therein, is incorporated by reference herein.

Selection of soybean plants for breeding is not necessarily dependent on the phenotype of a plant and instead can be based on genetic investigations. For example, one may utilize a suitable genetic marker which is closely genetically linked to a trait of interest. One of these markers may therefore be used to identify the presence or absence of a trait in the offspring of a particular cross, and hence may be used in selection of progeny for continued breeding. This technique may commonly be referred to as "marker assisted selection." Any other type of genetic marker or other assay which is able to identify the relative presence or absence of a trait of interest in a plant may also be useful for breeding purposes. Procedures for marker assisted selection applicable to the breeding of soybeans are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs), Restriction Fragment Length Polymorphisms (RFLPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), Simple Sequence Repeats (SSRs, also referred to as "Microsatellites"), and Single Nucleotide Polymorphisms (SNPs).

Many qualitative characters also have potential use as phenotype-based genetic markers in soybeans; however, some or many may not differ among varieties commonly used as parents. The most widely used genetic markers are flower color (purple dominant to white), pubescence color (brown dominant to gray), and pod color (brown dominant to tan). The association of purple hypocotyl color with purple flowers and green hypocotyl color with white flowers is commonly used to identify hybrids in the seedling stage. Differences in maturity, height, hilum color, pubescence color, pod wall color, and pest resistance between parents can also be used to verify hybrid plants.

Soybean variety SM14307266 represents a novel base genetic variety into which a new desired locus or trait may be introduced by introgression. Backcrossing and direct transformation represent two important methods that can be used to accomplish such an introgression. In certain embodiments of the present invention, plants of soybean variety SM14307266 are provided modified to include one or more desired heritable traits.

Plants of the subject invention including one or more desired heritable traits may, in one embodiment, be developed by a plant breeding technique called backcrossing, wherein essentially all of the desired physiological and morphological characteristics of a variety are recovered, when grown in the same environmental conditions, in addition to a genetic locus comprising the desired trait transferred into the plant via the backcrossing technique. Backcrossing methods can be used with the present invention to improve or introduce a desired trait into soybean variety SM14307266. The parental soybean plant which contributes the locus for the desired characteristic is termed the nonrecurrent or donor parent. This terminology refers to the fact that the nonrecurrent parent is used one time in the backcross protocol and therefore does not recur. The parental soybean plant (e.g., soybean variety SM14307266) to which the locus or loci from the nonrecurrent parent are transferred is known as the recurrent parent as it is used for several rounds in the backcrossing protocol (Poehlman et al., 1995; Fehr, 1987a,b; Sprague and Dudley, 1988).

In a typical backcross protocol, the original variety of interest (recurrent parent, e.g., soybean variety SM14307266) is crossed to a second variety (nonrecurrent parent) that carries the single locus of interest to be transferred to produce F1 progeny plants. The resulting F1 progeny from this cross are then selected that have the desired trait and crossed again to the recurrent parent to produce backcross progeny plants having the desired trait and physiological and morphological characteristics of the recurrent parent. The process is repeated until a soybean plant is obtained wherein essentially all of the desired morphological and physiological characteristics of the recurrent parent are recovered in the converted plant, in addition to the transferred locus comprising the desired trait from the nonrecurrent parent.

The selection of a suitable recurrent parent is an important step for a successful backcrossing procedure. The goal of a backcross protocol is to alter or substitute a single or a very limited number of traits or characteristics into the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Soybean varieties can also be developed from more than two parents (Fehr, In: *Soybeans: Improvement, Production and Uses,* 2d Ed., Monograph 16:249, 1987). The technique, known as modified backcrossing, uses different recurrent parents during the backcrossing. Modified backcrossing can be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, male sterility, herbicide tolerance, insect resistance, modified fatty acid metabolism, modified carbohydrate metabolism and resistance to bacterial disease, fungal disease or viral disease.

Direct selection may be applied where the single locus acts as a dominant trait. An example of a dominant trait is an herbicide tolerance trait. For this selection process, the progeny of the initial cross are sprayed with the herbicide prior to the backcrossing. The spraying eliminates any plants which do not have the desired herbicide tolerance characteristic, and only those plants which have the herbicide tolerance gene are used in the subsequent backcross. This process is then repeated for all additional backcross generations.

In other embodiments of the present invention, plants of the subject invention including one or more desired heritable traits may be developed by direct transformation of soybean variety SM14307266, or through the use of backcrossing approaches as described herein, for example, to introgress a transgenic trait into soybean variety SM14307266. Accordingly, in one embodiment of the present invention a method of producing a plant of soybean variety SM14307266 comprising an added desired trait is provided, where the method comprises introducing at least one transgene conferring the desired trait into variety SM14307266. In some embodiments, introducing at least one transgene conferring the desired trait comprises transforming a soybean plant, or part thereof, of variety SM14307266 with one or more transgenes that confer at least one desired trait. In another embodiment, introducing at least one transgene conferring the desired trait comprises use of backcrossing to introgress a transgenic trait into soybean variety SM14307266. Another embodiment is the product produced by this process, wherein the product comprises the at least one desired trait and all of the physiological and morphological characteristics of soybean variety SM14307266 when grown in the same location and in the same environmental conditions.

In one embodiment the desired trait may be one or more of male sterility, site-specific recombination, abiotic stress tolerance, herbicide tolerance, insect or pest resistance, disease resistance, fungal resistance, modified fatty acid metabolism, and modified carbohydrate metabolism. The specific gene may be any known in the art or listed herein, including: a polynucleotide conferring tolerance to glyphosate, phenoxyacetate auxins, pyridyloxyacetate auxins, phenoxyproprionate auxins, phenoxybutanoate auxins, sulfonylurea, imidazalinone, dicamba, glufosinate, cyclohexone, triazine, and benzonitrile; a polynucleotide encoding a *Bacillus thuringiensis* polypeptide (e.g. Cry1F and/or Cry1Ac), a polynucleotide encoding phytase, FAD-2, FAD-3, galactinol synthase or a raffinose synthetic enzyme; or a polynucleotide conferring resistance to soybean cyst nematode, brown stem rot, *phytophthora* root rot, soybean mosaic virus or sudden death syndrome.

Various genetic elements can be introduced into the plant genome using transformation. These elements include, but are not limited to: genes; coding sequences; inducible, constitutive, and tissue specific promoters; enhancing sequences; and signal and targeting sequences. For example, see the traits, genes and transformation methods listed in U.S. Pat. No. 6,118,055. The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

Plant transformation techniques which result in the generation of transgenic plants are known in the art. These techniques include, but are not limited to:

(1) Projectile bombardment or microprojectile-mediated delivery. This procedure involves propelling inert or biologically active particles complexed with DNA at plant cells, wherein the particles penetrate the outer surface of the cell and the DNA is incorporated within the genome of the plant cell. See e.g., Klein et al., (1987) Nature 327: 70-73; Tomes et al., Plant Cell, Tissue & Organ Culture: Fundamental Methods, eds. Gambourg and Phillips (1995) (Springer-Velag, Berlin); Gordon-Kim et al., (1990) Plant Cell 2:603-618; U.S. Pat. Nos. 4,945,050, 5,879,918, 5,932,782, 5,015,580, 5,550,318, 5,538,880, 6,160,208, 6,399,861, and 6,403,865;

(2) Microinjection of plant cell protoplasts or embryogenic callus, including the use of silicon carbide mediated DNA uptake. See e.g., Crossway et al., (1985) Molecular General Genetics 202:179; Kaeppler et al. (1990) Plant Cell Reporter 9:415-418;

(3) Direct gene transfer. See e.g., International Patent Application No. WO85/01856 and European Patent Application No. 0 275 069;

(4) Electroporation, calcium mediated, or PEG precipitation of protoplasts or cells comprising partial cell walls. See e.g., Fromm et al., (1985) Proceedings of the National Academy of Sciences 82: 5824; Paszkowski et al., (1984) European Molecular Biological Organization 3: 2717-2722; Potrykus et al. (1985) Molecular General Genetics 199:169-177; Shimamoto (1989) Nature 338:274-276; D'Halluin et al. (1992) Plant Cell 4: 1495-1505; and U.S. Pat. No. 5,384,253.

(5) Aerosol beam technology, which employs the jet expansion of an inert gas as it passes from a region of higher gas pressure to a region of lower gas pressure through a small orifice. The expanding gas accelerates aerosol droplets containing DNA molecules at supersonic speeds into a cell or tissue. See e.g., Held et al., U.S. Pat. Nos. 6,809,232; 7,067,716; and 7,026,286.

(6) *Agrobacterium*-mediated transformations of plants are also included. *Agrobacterium*-mediated transformation is described in, for example, Horsch et al., (1984) Science 233:496-498, and Fraley et al., (1983) *Proc. Nat. Acad. Sci. USA* 80:4803 and U.S. Pat. Nos. 5,824,877; 5,981,840, and 6,384,301; Ishida et al., (1996) Nature Biotechnology 14:745-750. Generally, the *Agrobacterium* transformation system is used to engineer dicotyledonous plants see Bevan et al (1982) *Ann. Rev. Genet* 16:357-384; Rogers et al., (1986) *Methods Enzymol.* 118:627-641). The *Agrobacterium* transformation system may also be used to transform, as well as transfer, DNA to monocotyledonous plants and plant cells. See U.S. Pat. No. 5,591,616; Hemalsteen et al., (1984) EMBO J 3:3039-3041; Hooykass-Van Slogteren et al., (1984) *Nature* 3 11: 763-764; Grimsley et al., (1987) *Nature* 325: 1677-179; Boulton et al., (1989) *Plant Mol. Biol.* 12:3 1-40; and Gould et al., (1991) *Plant Physiol.* 95:426-434. In addition, gene transfer may be achieved using non-*Agrobacterium* bacteria or viruses such as *Rhizobium* sp. NGR234, *Sinorhizobium meliloti, Mesorhizobium loti*, potato virus X, cauliflower mosaic virus and cassava vein mosaic virus and/or tobacco mosaic virus, See, e.g., Chung et al., (2006) Trends Plant Sci. 1 1(1): 1-4; U.S. Pat. Nos. 6,660,500, 6,462,255, 5,889,190 and 5,889,101.

Soybean transformation is described in particular in a number of publications. An example of an exemplary soybean transformation technique includes the use of *Agrobacterium*-mediated plant transformation. One example of soybean transformation comprises infecting half-seed explants of soybean with *Agrobacterium tumefaciens* containing a transgene and regenerating the half-seed explants in vitro on selection medium. See U.S. Pat. No. 7,473,822 and Paz et al., (2006) Plant Cell Reports 25: 206-213. A second example of *Agrobacterium*-mediated soybean transformation employs the use of glufosinate as the selection system, thereby resulting in an enhanced transformation efficiency. See Zeng et al., (2004) Plant Cell Rep 22:478-482.

After effecting delivery of exogenous DNA to recipient cells, the next steps generally concern identifying the transformed cells for further culturing and plant regeneration. In order to improve the ability to identify transformants, one may desire to employ a selectable or screenable marker gene with the transformation vector used to generate the transformant. In this case, the potentially transformed cell population can be assayed by exposing the cells to a selective agent or agents, or the cells can be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

To confirm the presence of a transgene in the regenerating plants, a variety of assays may be performed. Such assays include, for example: molecular biological assays, such as Southern and Northern blotting and PCR; biochemical assays, such as detecting the presence of a protein product, e.g., by immunological means (e.g., ELISA and/or Western blots) or by enzymatic function; plant part assays, such as leaf or root assays; and analysis of the phenotype of the whole regenerated plant.

Through the transformation of soybean, the expression of genes can be altered to enhance disease resistance, insect resistance, herbicide tolerance, agronomic, grain quality and other desired traits. Transformation can also be used to insert DNA sequences which control or help control male-sterility. DNA sequences native to soybean as well as non-native DNA sequences can be transformed into soybean and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing, or gene suppression) is desirable for several aspects of genetic engineering in plants.

Many techniques for gene silencing are well known to one of skill in the art, including but not limited to knock-outs (such as by insertion of a transposable element such as mu (Vicki Chandler, The Maize Handbook ch. 118 (Springer-Verlag 1994) or other genetic elements such as a FRT, Lox or other site specific integration site, antisense technology (see, e.g., Sheehy et al. (1988) PNAS USA 85:8805-8809; and U.S. Pat. Nos. 5,107,065; 5,453,566; and 5,759,829); co-suppression (e.g., Taylor (1997) Plant Cell 9:1245; Jorgensen (1990) Trends Biotech. 8(12):340-344; Flavell (1994) PNAS USA 91:3490-3496; Finnegan et al. (1994) Bio/Technology 12: 883-888; and Neuhuber et al. (1994) Mol. Gen. Genet. 244:230-241); RNA interference (Napoli et al. (1990) Plant Cell 2:279-289; U.S. Pat. No. 5,034,323; Sharp (1999) Genes Dev. 13:139-141; Zamore et al. (2000) Cell 101:25-33; and Montgomery et al. (1998) PNAS USA 95:15502-15507), virus-induced gene silencing (Burton, et al. (2000) Plant Cell 12:691-705; and Baulcombe (1999) Curr. Op. Plant Bio. 2:109-113); target-RNA-specific ribozymes (Haseloff et al. (1988) Nature 334: 585-591); hairpin structures (Smith et al. (2000) Nature 407:319-320; WO 99/53050; and WO 98/53083); MicroRNA (Aukerman & Sakai (2003) Plant Cell 15:2730-2741); ribozymes (Steinecke et al. (1992) EMBO J. 11:1525; and Perriman et al. (1993) Antisense Res. Dev. 3:253); oligonucleotide-mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

Exemplary nucleotide sequences or encoded polypeptides that may be altered or introduced by genetic engineering to provide desired traits include, but are not limited to, those categorized below.

1. Genes or Encoded Proteins that Confer Resistance to Pests or Disease.

(A) Plant Disease Resistance Genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. Examples of such genes include, the tomato Cf-9 gene for resistance to *Cladosporium flavum* (Jones et al., 1994 Science 266:789), tomato Pto gene, which encodes a protein kinase, for resistance to *Pseudomonas syringae* pv. tomato (Martin et al., 1993 Science 262:1432), and *Arabidopsis* RSSP2 gene for resistance to *Pseudomonas syringae* (Mindrinos et al., 1994 Cell 78:1089).

(B) A *Bacillus thuringiensis* protein, a derivative thereof or a synthetic polypeptide modeled thereon, such as, a nucleotide sequence of a Bt δ-endotoxin gene (Geiser et al., 1986 Gene 48:109). Moreover, DNA molecules encoding δ-endotoxin genes can be purchased from American Type Culture Collection (Rockville, Md.), under ATCC accession numbers, e.g., 40098, 67136, 31995 and 31998. Other non-limiting examples of *Bacillus thuringiensis* transgenes being genetically engineered are given in the following patents, patent applications and publications and hereby are incorporated by reference for this purpose: U.S. Pat. Nos. 5,188,960; 5,689,052; 5,880,275; 5,986,177; 7,105,332; 7,208,474; WO 91/14778; WO 99/31248; WO 01/12731; WO 99/24581; WO 97/40162 and U.S. application Ser. Nos. 10/032,717; 10/414,637; 11/018,615; 11/404,297; 11/404,638; 11/471,878; 11/780,501; 11/780,511; 11/780,503; 11/953,648; 11/953,648; and Ser. No. 11/957,893, and Estruch, et al., 1996. Proc. Natl. Acad. Sci. 93:5389.

(C) A lectin, such as, nucleotide sequences of several *Clivia miniata* mannose-binding lectin genes (Van Damme et al., 1994 Plant Molec. Biol. 24:825).

(D) A vitamin binding protein, such as avidin and avidin homologs which are useful as larvicides against insect pests. See U.S. Pat. No. 5,659,026.

(E) An enzyme inhibitor, e.g., a protease inhibitor or an amylase inhibitor. Examples of such genes include, a rice cysteine proteinase inhibitor (Abe et al., 1987 J. Biol. Chem. 262:16793), a tobacco proteinase inhibitor I (Huub et al., 1993 Plant Molec. Biol. 21:985), and an α-amylase inhibitor Sumitani et al., 1993 Biosci. Biotech. Biochem. 57:1243).

(F) An insect-specific hormone or pheromone such as an ecdysteroid and juvenile hormone a variant thereof, a mimetic based thereon, or an antagonist or agonist thereof, such as, baculovirus expression of cloned juvenile hormone esterase, an inactivator of juvenile hormone (Hammock et al., 1990 Nature 344:458).

(G) An insect-specific peptide or neuropeptide which, upon expression, disrupts the physiology of the affected pest. Examples of such genes include, an insect diuretic hormone receptor (Regan, 1994), an allostatin identified in *Diploptera punctata* (Pratt, 1989), insect-specific, paralytic neurotoxins (U.S. Pat. No. 5,266,361).

(H) An insect-specific venom produced in nature by a snake, a wasp, etc., such as, a scorpion insectotoxic peptide (Pang, 1992 Gene 116:165).

(I) An enzyme responsible for a hyperaccumulation of monoterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. Examples of such genes include, a callas gene (PCT published application WO93/02197), chitinase-encoding sequences (which can be obtained, for example, from the ATCC under accession numbers 3999637 and 67152), tobacco hookworm chitinase (Kramer et al., 1993 Insect Molec. Biol. 23:691) and parsley ubi4-2 polyubiquitin gene (Kawalleck et al., 1993 Plant Molec. Biol. 21:673).

(K) A molecule that stimulates signal transduction. Examples of such molecules include, nucleotide sequences for mung bean calmodulin cDNA clones (Botella et al., 1994 Plant Molec. Biol. 24:757) and a nucleotide sequence of a maize calmodulin cDNA clone (Griess et al., 1994 Plant Physiol. 104:1467).

(L) A hydrophobic moment peptide. See U.S. Pat. Nos. 5,659,026 and 5,607,914, the latter teaches synthetic antimicrobial peptides that confer disease resistance.

(M) A membrane permease, a channel former or a channel blocker, such as, a cecropin-β lytic peptide analog (Jaynes et al., 1993 Plant Sci. 89:43) which renders transgenic tobacco plants resistant to *Pseudomonas solanacearum*.

(N) A viral-invasive protein or a complex toxin derived there from. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. See, for example, Beachy et al. (1990) Ann. Rev. Phytopathol. 28:451.

(O) An insect-specific antibody or an immunotoxin derived therefrom. Thus, an antibody targeted to a critical metabolic function in the insect gut would inactivate an affected enzyme, killing the insect. For example, Taylor et al. (1994) Abstract #497, Seventh Int'l. Symposium on Molecular Plant-Microbe Interactions, shows enzymatic inactivation in transgenic tobacco via production of single-chain antibody fragments.

(P) A virus-specific antibody. See, for example, Tavladoraki et al. (1993) Nature 266:469, which shows that transgenic plants expressing recombinant antibody genes are protected from virus attack.

(Q) A developmental-arrestive protein produced in nature by a pathogen or a parasite. Thus, fungal endo α-1,4-D polygalacturonases facilitate fungal colonization and plant nutrient release by solubilizing plant cell wall homo-α-1,4-D-galacturonase (Lamb et al., 1992) Bio/Technology 10:1436. The cloning and characterization of a gene which encodes a bean endopolygalacturonase-inhibiting protein is described by Toubart et al. (1992 Plant J. 2:367).

(R) A developmental-arrestive protein produced in nature by a plant, such as, the barley ribosome-inactivating gene has an increased resistance to fungal disease (Longemann et al., 1992). Bio/Technology 10:3305.

(S) A small RNA (e.g., antisense, hairpin, siRNA, or miRNA) that inhibits expression of a pathogen gene necessary for the pathogen to survive or thrive.

2. Genes that Confer Tolerance to a Herbicide.

(A) Genes encoding resistance or tolerance to a herbicide that inhibits the growing point or meristem, such as an imidazalinone or a sulfonylurea. Exemplary genes in this category code for mutant ALS (Lee et al., 1988 EMBOJ. 7:1241) and AHAS enzyme (Miki et al., 1990 Theor. Appl. Genet. 80:449).

(B) One or more additional genes encoding resistance or tolerance to glyphosate imparted by mutant EPSP synthase and aroA genes, or through metabolic inactivation by genes such as GAT (glyphosate acetyltransferases or GOX (glyphosate oxidase) and other phosphono compounds such as glufosinate (PAT and bar genes), and pyridinoxy or phenoxy proprionic acids and cyclohexones (ACCase inhibitor encoding genes). See, for example, U.S. Pat. No. 4,940,835, which discloses the nucleotide sequence of a form of EPSP which can confer glyphosate tolerance. A DNA molecule encoding a mutant aroA gene can be obtained under ATCC accession number 39256, and the nucleotide sequence of the mutant gene is disclosed in U.S. Pat. No. 4,769,061. European patent application No. 0 333 033 and U.S. Pat. No. 4,975,374 disclose nucleotide sequences of glutamine synthetase genes which confer tolerance to herbicides such as L-phosphinothricin. The nucleotide sequence of a phosphinothricinacetyl-transferase gene is provided in European application No. 0 242 246. De Greef et al. (1989) Bio/Technology 7:61 describes the production of transgenic plants that express chimeric bar genes coding for phosphinothricin acetyl transferase activity. Exemplary genes conferring tolerance to phenoxy proprionic acids and cyclohexones, such as sethoxydim and haloxyfop, are the Accl-S1, Accl-S2 and Accl-S3 genes described by Marshall et al. (1992) Theor. Appl. Genet. 83:435.

(C) Genes encoding resistance or tolerance to a herbicide that inhibits photosynthesis, such as a triazine (psbA and gs+ genes) and a benzonitrile (nitrilase gene). Przibilla et al. (1991) Plant Cell 3:169 describes the use of plasmids encoding mutant psbA genes to transform Chlamydomonas. Nucleotide sequences for nitrilase genes are disclosed in U.S. Pat. No. 4,810,648, and DNA molecules containing these genes are available under ATCC accession numbers 53435, 67441 and 67442. Cloning and expression of DNA coding for a glutathione S-transferase is described by Hayes et al. (1992) Biochem. J. 285:173.

(D) Genes encoding resistance or tolerance to a herbicide that bind to hydroxyphenylpyruvate dioxygenases (HPPD), enzymes which catalyze the reaction in which para-hydroxyphenylpyruvate (HPP) is transformed into homogentisate. This includes herbicides such as isoxazoles (EP418175, EP470856, EP487352, EP527036, EP560482, EP682659, U.S. Pat. No. 5,424,276), in particular isoxaflutole, which is a selective herbicide for maize, diketonitriles (EP496630, EP496631), in particular 2-cyano-3-cyclopropyl-1-(2-SO2CH3-4-CF3 phenyl)propane-1,3-dione and 2-cyano-3-cyclopropyl-1-(2-SO2CH3-4-2,3Cl2phenyl)propane-1,3-dione, triketones (EP625505, EP625508, U.S. Pat. No. 5,506, 195), in particular sulcotrione, or else pyrazolinates. A gene that produces an overabundance of HPPD in plants can provide tolerance or resistance to such herbicides, including, for example, genes described at U.S. Pat. Nos. 6,268,549 and 6,245,968 and U.S. publication No. 20030066102.

(E) Genes encoding resistance or tolerance to phenoxyacetate auxin herbicides, such as 2, 4-dichlorophenoxyacetic acid (2,4-D) and which may also confer resistance or tolerance to "fop" herbicides. Examples of such genes include the α-ketoglutarate-dependent dioxygenase enzyme (AAD-1) gene, described at U.S. Pat. No. 7,838,733.

(F) Genes encoding resistance or tolerance to phenoxyacetate auxin herbicides, such as 2, 4-dichlorophenoxyacetic acid (2,4-D) and which may also confer resistance or tolerance to pyridyloxyacetate auxins (such as fluroxypyr and triclopyr), phenoxypropionate auxins (such as MCPA and dichloprop), phenoxybutanoate auxins (such as 2,4-DB). Examples of such genes include the α-ketoglutarate-dependent dioxygenase enzyme (AAD-12) gene, described in U.S. Pat. No. 8,283,522.

(G) Genes encoding resistance or tolerance to dicamba, such as dicamba monooxygenase (DMO) from Pseudomonas maltophilia which is involved in the conversion of a herbicidal form of the herbicide dicamba to a non-toxic 3,6-dichlorosalicylic acid and thus may be used for producing plants tolerant to this herbicide. See, e.g., U.S. Patent Application No: 20030135879.

3. Genes that Confer or Contribute to a Value-Added Trait.

(A) Modified fatty acid metabolism, for example, by transforming maize or Brassica with a small RNA or stearoyl-ACP desaturase to increase stearic acid content of the plant (Knultzon et al., 1992) Proc. Nat. Acad. Sci. USA 89:2624.

(B) Decreased Phytate Content (1) Introduction of a phytase-encoding gene would enhance breakdown of phytate, adding more free phosphate to the transformed plant, such as the Aspergillus niger phytase gene (Van Hartingsveldt et al., 1993 Gene 127:87).

(2) A gene could be introduced that reduces phytate content. In maize, this, for example, could be accomplished by cloning and then reintroducing DNA associated with the single allele which is responsible for maize mutants characterized by low levels of phytic acid (Raboy et al., 1990 Maydica 35:383).

(C) Modified carbohydrate composition effected, for example, by transforming plants with a gene coding for an enzyme that alters the branching pattern of starch. Examples of such enzymes include, Streptococcus mucus fructosyltransferase gene (Shiroza et al., 1988) J. Bacteriol. 170:810, *Bacillus subtilis* levansucrase gene (Steinmetz et al., 1985 Mol. Gen. Genel. 200:220), *Bacillus licheniformis* α-amylase (Pen et al., 1992 Bio/Technology 10:292), tomato invertase genes (Elliot et al., 1993), barley amylase gene (Sogaard et al., 1993 J. Biol. Chem. 268:22480), and maize endosperm starch branching enzyme II (Fisher et al., 1993 Plant Physiol. 102:1045).

(D) Altered antioxidant content or composition, such as alteration of tocopherol or tocotrienols. For example, see U.S. Pat. No. 6,787,683, US2004/0034886 and WO 00/68393 involving the manipulation of antioxidant levels, and WO 03/082899 through alteration of a homogentisate geranyl geranyl transferase (HGGT).

(E) Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO 99/40209 (alteration of amino acid compositions in seeds), WO 99/29882 (methods for altering amino acid content of proteins), U.S. Pat. No. 5,850,016 (alteration of amino acid compositions in seeds), WO 98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO 98/56935 (plant amino acid biosynthetic enzymes), WO 98/45458 (engineered seed protein having higher percentage of essential amino acids), WO 98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO 96/01905 (increased threonine), WO 95/15392 (increased lysine), US2003/0163838, US2003/0150014, US2004/0068767, U.S. Pat. No. 6,803,498, WO 01/79516.

4. Genes that Control Male-Sterility.

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum-specific promoter and with the application of the chemical N—Ac-PPT (WO 01/29237).

(B) Introduction of various stamen-specific promoters (WO 92/13956, WO 92/13957).

(C) Introduction of the barnase and the barstar gene (Paul et al. Plant Mol. Biol. 19:611-622, 1992).

For additional examples of nuclear male and female sterility systems and genes, see also, U.S. Pat. Nos. 5,859,341; 6,297,426; 5,478,369; 5,824,524; 5,850,014; and 6,265,640; all of which are hereby incorporated by reference.

5. Genes that affect abiotic stress resistance (including but not limited to enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO 00/060089, WO 01/026459, WO 01/035725, WO 01/034726, WO 01/035727, WO 01/036444, WO 01/036597, WO 01/036598, WO 02/015675, WO 02/017430, WO 02/079403, WO 03/013227, WO 03/013228, WO 03/014327, WO 04/031349, WO 04/076638, WO 98/09521, and WO 99/38977 describing genes, including CBF genes and transcription factors effective in mitigating the negative effects of freezing, high salinity, and drought on plants, as well as conferring other positive effects on plant phenotype; US2004/0148654 and WO 01/36596 where abscisic acid is altered in plants resulting in improved plant phenotype such as increased yield and/or increased tolerance to abiotic stress; WO 00/006341, WO 04/090143, U.S. application Ser. Nos. 10/817,483 and 09/545,334 where cytokinin expression is modified resulting in plants with increased stress tolerance, such as drought tolerance, and/or increased yield. Also see WO 02/02776, WO 03/052063, JP2002281975, U.S. Pat. No. 6,084,153, WO 01/64898, U.S. Pat. Nos. 6,177,275, and 6,107,547 (enhancement of nitrogen utilization and altered nitrogen responsiveness). For ethylene alteration, see US2004/0128719, US2003/0166197 and WO 00/32761. For plant transcription factors or transcriptional regulators of abiotic stress, see e.g. US2004/0098764 or US2004/0078852.

Other genes and transcription factors that affect plant growth and agronomic traits such as yield, flowering, plant growth and/or plant structure, can be introduced or introgressed into plants, see e.g. WO 97/49811 (LHY), WO 98/56918 (ESD4), WO 97/10339 and U.S. Pat. No. 6,573,430 (TFL), U.S. Pat. No. 6,713,663 (FT), WO 96/14414 (CON), WO 96/38560, WO 01/21822 (VRN1), WO 00/44918 (VRN2), WO 99/49064 (GI), WO 00/46358 (FRI), WO 97/29123, U.S. Pat. Nos. 6,794,560, 6,307,126 (GAI), WO 99/09174 (D8 and Rht), and WO 04/076638 and WO 04/031349 (transcription factors).

One may obtain soybean plants according to the present invention by directly growing the seed of SM14307266 or by any other means. A soybean plant having all of the physiological and morphological characteristics of SM14307266 can be obtained by any suitable means, including, but not limited to, regenerating plants or plant parts from tissue culture or cuttings. The scope of the present invention is not limited by the method by which the plant is obtained.

Tissue Cultures and Plants Regenerated Therefrom

The present invention provides a tissue culture of protoplasts or regenerable cells from a plant, or parts thereof, produced from soybean variety SM14307266, or a part thereof. In some embodiments, the protoplasts or regenerable cells are derived from embryo, meristematic cell, leaf, pollen, ovule, cotyledon, hypocotyl, embryo, root, root tip, anther, pistil, pod, flower, shoot or stalk of soybean variety SM14307266.

Tissue culture of various tissues of soybeans and regeneration of plants therefrom is well known and widely published. For example, reference may be had to Komatsuda, T. et al., "Genotype X Sucrose Interactions for Somatic Embryogenesis in Soybean," Crop Sci. 31:333-337 (1991); Stephens, P. A. et al., "Agronomic Evaluation of Tissue-Culture-Derived Soybean Plants," Theor. Appl. Genet. (1991) 82:633-635; Komatsuda, T. et al., "Maturation and Germination of Somatic Embryos as Affected by Sucrose and Plant Growth Regulators in Soybeans *Glycine gracilis* Skvortz and *Glycine max* (L.) Merr.," Plant Cell, Tissue and Organ Culture, 28:103-113 (1992); Dhir, S. et al., "Regeneration of Fertile Plants from Protoplasts of Soybean (*Glycine max* L. Merr.): Genotypic Differences in Culture Response," Plant Cell Reports (1992) 11:285-289; Pandey, P. et al., "Plant Regeneration from Leaf and Hypocotyl Explants of *Glycine wightii* (W. and A.) VERDC. var. *longicauda*," Japan J. Breed. 42:1-5 (1992); and Shetty, K., et al., "Stimulation of In Vitro Shoot Organogenesis in *Glycine max* (Merrill.) by Allantoin and Amides," Plant Science 81: (1992) 245-251; as well as U.S. Pat. No. 5,024,944, issued Jun. 18, 1991 to Collins et al. and U.S. Pat. No. 5,008,200, issued Apr. 16, 1991 to Ranch et al., the disclosures of which are hereby incorporated herein in their entirety by reference. Thus, another aspect of the present invention is to provide cells which upon growth and differentiation produce soybean plants having the physiological and morphological characteristics of soybean variety SM14307266.

Soybean Products

Soybean is useful not only as a seed for producing soybean plants, but also has utility as a grain. The grain can be used as a food source for both animals and humans. Soybean is widely used as a source of protein for animal feeds for poultry, swine and cattle. The soybean grain is therefore a commodity. The soybean commodity plant products include but are not limited to protein concentrate, protein isolate, soybean hulls, meal, flower, oil and the whole soybean itself.

During processing of whole soybeans, the fibrous hull is removed and the oil is extracted. The remaining soybean meal is a combination of carbohydrates and approximately 50% protein. For human or animal consumption soybean meal is made into soybean flour that is processed to protein concentrates used for meat extenders or specialty pet foods. Production of edible protein ingredients from soybean offers a healthy less expensive replacement for animal protein in meats as well as dairy-type products.

Accordingly, the present invention includes in some embodiments methods for producing a commodity plant product, which comprise obtaining seed of soybean variety SM14307266 and producing the commodity plant products disclosed above. The invention further comprises soybean commodity plant products derived from soybean variety SM14307266 seed according to these methods.

Deposit Information

Seed from soybean variety SM14307266, disclosed above and recited in the appended claims, is irrevocably deposited under the Budapest Treaty with the American Type Culture Collection (ATCC), 10801 University Boulevard, Manassas, Va. 20110 on Nov. 22, 2016 and having ATCC deposit number PTA-123574. The seeds deposited were taken from seeds maintained by Applicant since prior to the filing date of this application. Access to the ATCC deposit will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C.F.R. § 1.808 by affording access to the deposit with the ATCC. Applicant has or will have satisfied all of the requirements of 37 C.F.R. §§ 1.801-1.809. The deposit will be maintained in the ATCC depository for a period of 30 years, or 5 years after the last request, or for the effective life of the patent, whichever is longer, and will be replaced if necessary during that period.

All publications, patents and patent applications referenced in the specification are indicative of the level of those skilled in the art to which this invention pertains. All such publications, patents and patent applications are incorporated by reference herein to the same extent as if each was specifically and individually indicated to be incorporated by reference herein.

The foregoing invention has been described in some detail by way of illustration and example for purposes of clarity and understanding. However, it should be appreciated by those having ordinary skill in the art that certain changes and modifications such as single gene modifications and mutations, somoclonal variants, variant individuals selected from large populations of the plants of the instant novel variety and the like may be practiced within the scope of the invention, as limited only by the scope of the appended claims, without departing from the true concept, spirit, and scope of the invention.

What is claimed is:

1. A seed of soybean variety SM14307266, wherein a representative sample of the seed having been deposited under ATCC Accession No. PTA-123574.

2. A plant of soybean variety SM14307266, or a part thereof, wherein representative seed of said soybean variety SM14307266 having been deposited under ATCC Accession No. PTA-123574.

3. The plant part of claim 2, wherein the part is a pollen grain, an ovule, a protoplast, a cell, an embryo, a cotyledon, a hypocotyl, a meristem, a root, a pistil, an anther, a flower, a stem, a pod, a leaf or a petiole.

4. A soybean plant, or a part thereof, having all the physiological and morphological characteristics of the soybean plant of claim 2 when grown in the same environmental conditions.

5. A tissue culture of protoplasts or regenerable cells from the plant, or a part thereof, of claim 2.

6. The tissue culture of protoplasts or regenerable cells of claim 5, wherein the protoplasts or regenerable cells are derived from embryo, meristematic cell, leaf, pollen, ovule, cotyledon, hypocotyl, root, root tip, anther, pistil, pod, flower, shoot or stalk.

7. A soybean plant regenerated from the tissue culture of claim 6, wherein the plant has all of the physiological and morphological characteristics of a plant produced by growing seed of soybean variety SM14307266 under the same environmental conditions, and wherein a representative sample of the seed having been deposited under ATCC Accession No. PTA-123574.

8. A method for producing a soybean seed, said method comprising the steps of crossing soybean plants and harvesting the resultant seed, wherein at least one soybean plant is the soybean plant of claim 2.

9. An F1 hybrid soybean seed produced by the method of claim 8.

10. An F1 hybrid soybean plant produced by growing the seed of claim 9.

11. A method for producing a soybean variety SM14307266-derived soybean plant, said method comprising the steps of:
   (a) crossing the soybean variety SM14307266 plant of claim 2 with a second soybean plant to yield progeny soybean seed; and
   (b) growing said progeny seed to yield a soybean variety SM14307266-derived soybean plant.

12. An F1 soybean variety SM14307266-derived soybean plant produced by the method of claim 11.

13. The method of claim 11, further comprising the steps of:
   (c) crossing the soybean variety SM14307266-derived soybean plant of (b) with itself or another soybean plant to yield an additional soybean variety SM14307266-derived soybean progeny seed; and
   (d) growing the progeny soybean seed of (c) to yield additional soybean variety SM14307266-derived soybean plants.

14. The method of claim 13, wherein (c) and (d) are repeated at least one time to generate additional soybean variety SM14307266-derived soybean plants.

15. A method of making a plant of soybean variety SM14307266 comprising an added desired trait, the method comprising the step of introducing at least one transgene or locus conferring the desired trait into the plant of claim 2.

16. The method of claim 15, wherein the desired trait is selected from the group consisting of male sterility, site-specific recombination, abiotic stress tolerance, herbicide tolerance, insect or pest resistance, disease resistance, fungal resistance, modified fatty acid metabolism, and modified carbohydrate metabolism.

17. The method of claim 16, wherein the desired trait is herbicide tolerance and the tolerance is conferred to one or more herbicides selected from the group consisting of glyphosate, phenoxyacetate auxins, pyridyloxyacetate auxins, phenoxyproprionate auxins, phenoxybutanoate auxins, sulfonylurea, imidazalinone, dicamba, glufosinate, cyclohexone, triazine, and benzonitrile.

18. The method of claim 16, wherein the desired trait is insect resistance and the transgene encodes a *Bacillus thuringiensis* (Bt) endotoxin.

19. A plant produced by the method of claim 15, wherein the plant comprises the desired trait and all of the physiological and morphological characteristics of soybean variety SM14307266 when grown in the same environmental conditions, and wherein a representative sample of seed of said soybean variety SM14307266 having been deposited under ATCC Accession No. PTA-123574.

20. A method of producing a progeny soybean variety derived from variety SM14307266 comprising a desired trait, said method comprising the steps of:
   (a) crossing the soybean variety SM14307266 plant of claim 2 with a plant of another soybean variety that comprises a desired trait to produce F1 progeny plants;
   (b) selecting one or more F1 progeny plants that have the desired trait to produce selected progeny plants;
   (c) crossing the selected progeny plants with the soybean variety SM14307266 plant to produce backcross progeny plants;
   (d) selecting for backcross progeny plants that have the desired trait and physiological and morphological characteristics of the soybean variety SM14307266 plant to produce selected backcross progeny plants; and
   (e) repeating steps (c) and (d) a sufficient number of times in succession to produce selected second or higher backcross progeny plants that comprise the desired trait and all of the physiological and morphological characteristics of soybean variety SM14307266 when grown in the same environmental conditions.

21. The method of claim 20, wherein the desired trait is selected from the group consisting of male sterility, herbicide tolerance, insect resistance, modified fatty acid metabolism, modified carbohydrate metabolism and resistance to bacterial disease, fungal disease or viral disease.

22. A plant produced by the method of claim 20, wherein the plant has the desired trait and all of the other physiological and morphological characteristics of soybean variety SM14307266 when grown in the same environmental conditions, and wherein a representative sample of seed of said soybean variety SM14307266 having been deposited under ATCC Accession No. PTA-123574.

23. A method of producing a commodity plant product comprising the steps of obtaining the plant of claim 2, or a part thereof, and producing said commodity plant product therefrom.

24. The method of claim 23, wherein the commodity plant product is protein concentrate, protein isolate, soybean hulls, meal, flour or oil.

* * * * *